United States Patent
Carlson

(10) Patent No.: US 6,190,480 B1
(45) Date of Patent: Feb. 20, 2001

(54) METHOD OF MAKING A DOUBLE-WALLED FLEXIBLE TUBING PRODUCT WITH HELICAL SUPPORT BEAD AND HEATING CONDUCTOR

(75) Inventor: Lennart L. Carlson, Newport Coast, CA (US)

(73) Assignee: Steward Plastics, Inc., Laguna Hills, CA (US)

( * ) Notice: Under 35 U.S.C. 154(b), the term of this patent shall be extended for 0 days.

(21) Appl. No.: 09/160,803

(22) Filed: Sep. 25, 1998

Related U.S. Application Data

(60) Division of application No. 08/759,487, filed on Dec. 5, 1996, now Pat. No. 5,848,223, which is a continuation-in-part of application No. 08/507,732, filed on Jul. 26, 1995, now Pat. No. 5,637,168, which is a division of application No. 08/250,173, filed on May 27, 1994, now Pat. No. 5,454,061.

(51) Int. Cl.[7] .................................................. B65H 81/00
(52) U.S. Cl. ..................... 156/143; 156/187; 156/188; 156/190; 156/195; 156/244.13
(58) Field of Search .................................... 156/195, 143, 156/185, 187, 188, 190, 244.13

(56) References Cited

U.S. PATENT DOCUMENTS

| | | |
|---|---|---|
| Re. 29,332 | 8/1977 | Bilbro et al. . |
| 3,889,716 * | 6/1975 | Linhart .................................. 138/129 |
| 3,908,704 | 9/1975 | Clement et al. . |
| 3,910,713 | 10/1975 | Maroschak . |
| 3,910,808 | 10/1975 | Steward . |
| 3,914,146 | 10/1975 | Koch . |
| 3,914,147 | 10/1975 | Wienand et al. . |
| 3,917,500 | 11/1975 | Petzentakis et al. . |
| 3,919,026 | 11/1975 | Mizutani et al. . |
| 3,963,856 | 6/1976 | Carlson et al. . |
| 3,996,323 | 12/1976 | Hegler et al. . |
| 4,038,519 | 7/1977 | Foucras . |
| 4,118,453 | 10/1978 | Herrington . |
| 4,120,628 | 10/1978 | Simos . |
| 4,134,958 | 1/1979 | Dunichev et al. . |
| 4,165,214 | 8/1979 | Lupke et al. . |
| 4,166,000 | 8/1979 | Lawson . |
| 4,490,575 * | 12/1984 | Kutnyak .......................... 138/129 X |
| 4,553,023 | 11/1985 | Jameson et al. . |
| 4,667,084 | 5/1987 | Regge . |
| 4,686,354 | 8/1987 | Makin . |
| 4,731,138 * | 3/1988 | Lupke ............................. 156/195 X |
| 4,952,793 | 8/1990 | Cantrell et al. . |
| 5,089,074 * | 2/1992 | Winter et al. .................... 156/244.13 |
| 5,129,429 * | 7/1992 | Winter et al. ......................... 138/121 |
| 5,454,061 * | 9/1995 | Carlson ................................. 392/478 |

FOREIGN PATENT DOCUMENTS

| | | |
|---|---|---|
| 448933 | 3/1993 | (EP) . |
| 424493 | 10/1996 | (EP) . |
| 683259 | 10/1998 | (EP) . |

* cited by examiner

*Primary Examiner*—Jeff H. Aftergut
(74) *Attorney, Agent, or Firm*—Terry L. Miller

(57) ABSTRACT

A flexible double-walled plastic tubing product includes a helically wound support bead between inner and outer walls, and an helically wrapped electrical resistance heating conductor is disposed adjacent to the inner wall in good heat transfer relation to fluid flow within the tubing product. Fluid flow within the tubing product is insulated against heat loss to ambient by the helical support bead and a trapped "dead-air" space between the walls of the tubing product. Apparatus and method for making the tubing product are disclosed.

22 Claims, 6 Drawing Sheets

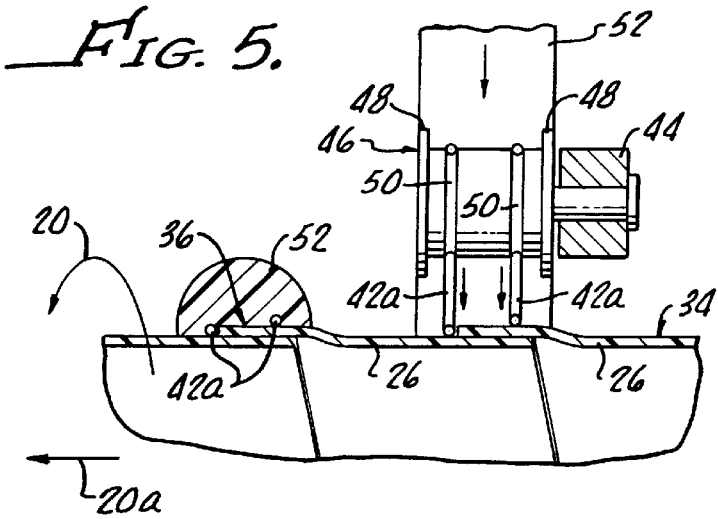
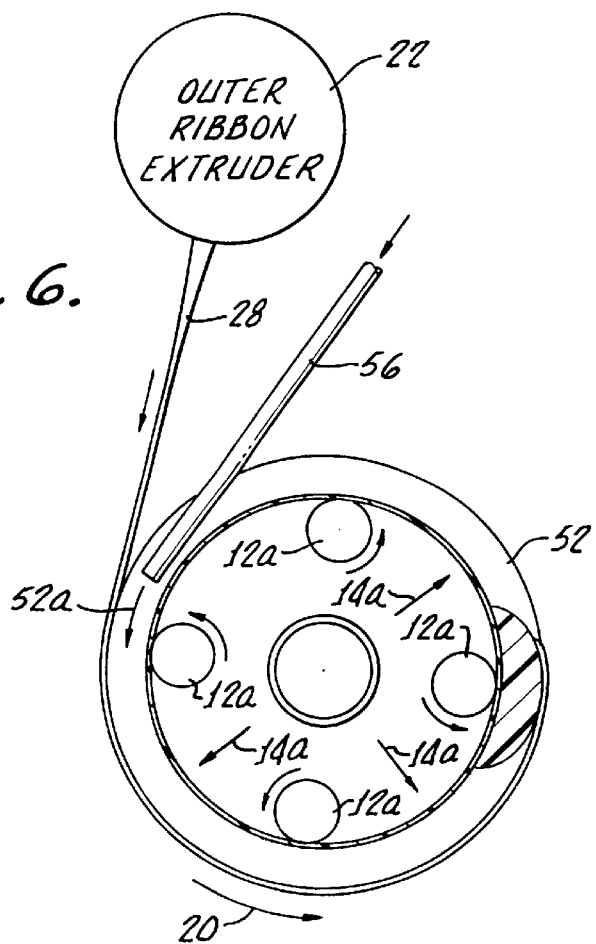

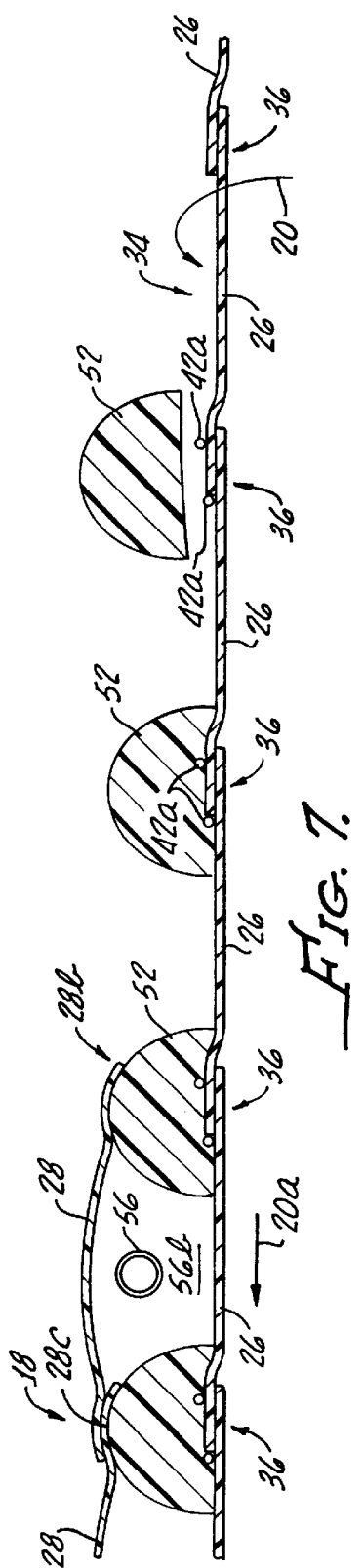
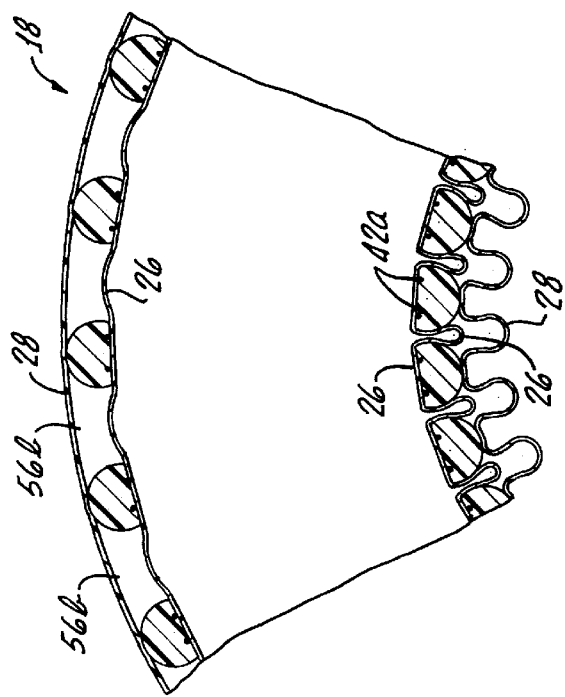
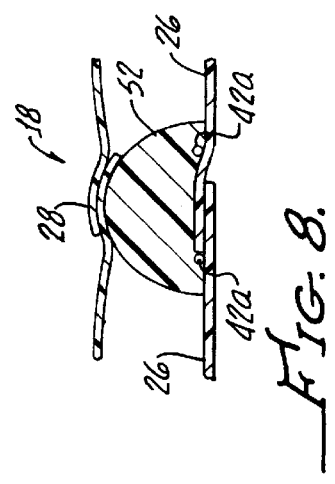
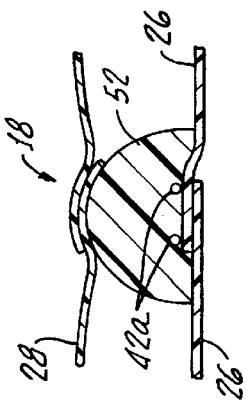

Fig. 11.
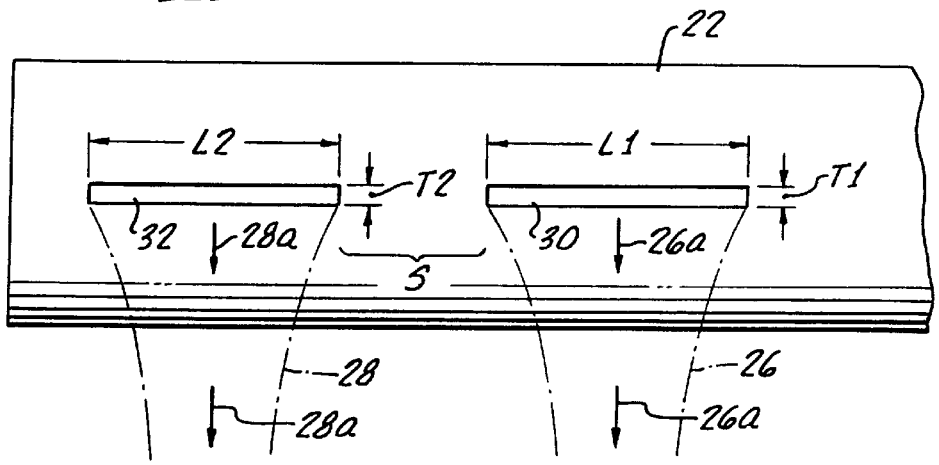
Fig. 12.
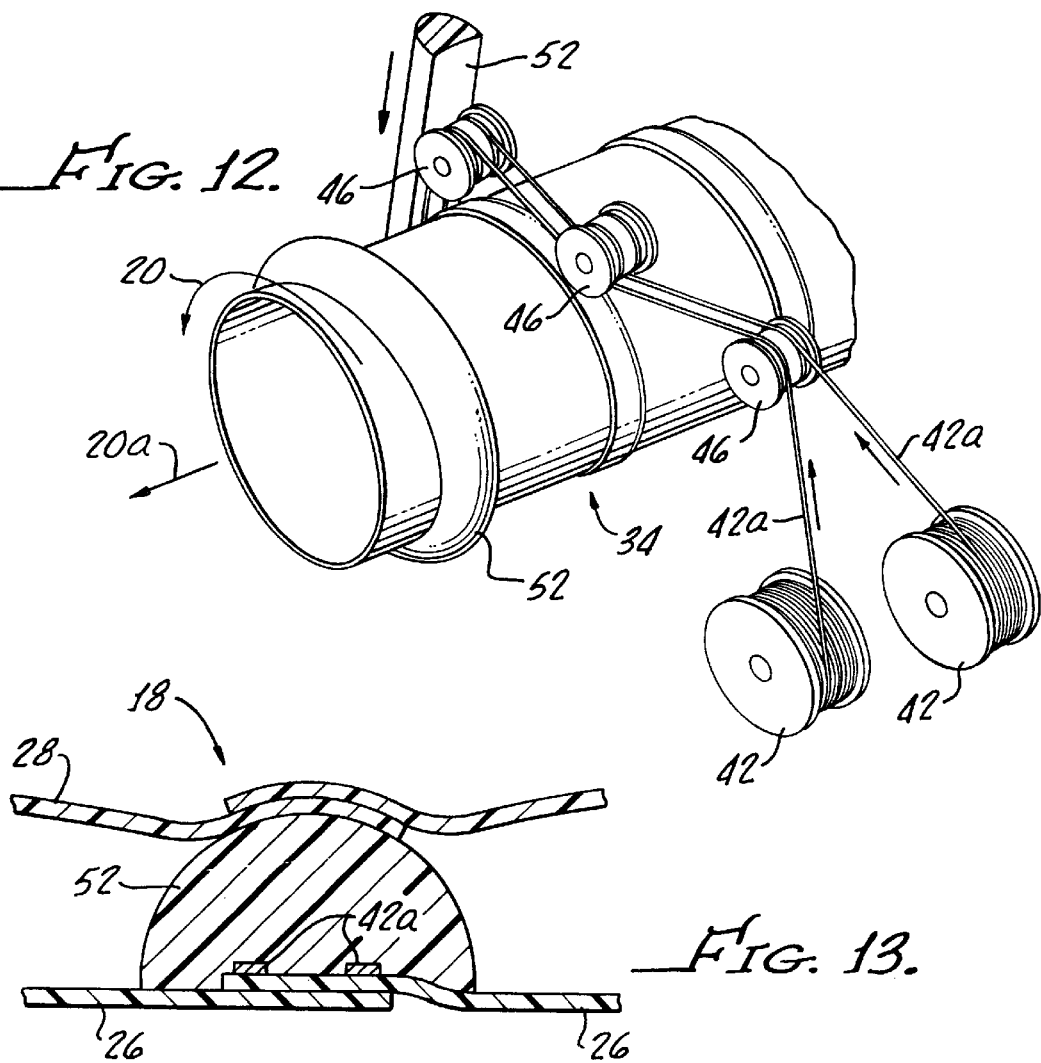
Fig. 13.

METHOD OF MAKING A DOUBLE-WALLED FLEXIBLE TUBING PRODUCT WITH HELICAL SUPPORT BEAD AND HEATING CONDUCTOR

RELATED APPLICATIONS

This application is a divisional of U.S. patent application Ser. No. 08/759,487 filed Dec. 5, 1996 now U.S. Pat. No. 5,848,223; which is a continuation-in-part application of U.S. patent application Ser. No. 08/507,732, filed Jul. 26, 1995 now U.S. Pat. No. 5,637,168, issued Jul. 10, 1997; which is a divisional application of U.S. patent application Ser. No. 08/250,173, filed on May 27, 1994, now U.S. Pat. No. 5,454,061, issued Sep. 26, 1995.

BACKGROUND OF THE INVENTION

1. Field of the Invention

The present invention relates in general to flexible plastic tubing and, more particularly, to apparatus and methods for making double-walled flexible plastic tubing having a helical support bead and integrally incorporating at least one electrical resistance heating conductor. Still more particularly, the present invention relates to a flexible double-walled and electrically-heated plastic tubing having a greatly reduced rate of heat loss compared to conventional single-walled tubing of this type. The present tubing further is configured to maintain a substantially smooth bore even when bent.

2. Description of Related Art

Throughout this disclosure, it will be recalled that heat transfer in a body, or between the interior of a body and ambient (i.e., heat loss from within a body to ambient) may be considered either from the standpoint of heat transfer conductivity (C) (a measure of heat transfer quantity per unit of area per degree of temperature difference), or in terms of heat transfer resistivity (i.e., the familiar "R" rating frequently used on building insulation products, for example). The "R" value is simply the reciprocal of heat transfer conductivity (i.e., R=1/C). Thus, these concepts and values may be used interchangeably, with allowance for the reciprocal relationship of the values.

Conventional flexible, thin-walled, helically-corrugated tubing having a relatively thin single wall and an integral helical supporting bead is known in the art. Such support-bead tubing construction provides substantial crush resistance while leaving the tube wall flexible enough to permit short-radius bends without collapsing or kinking the tube. The versatility of this kind of tubing is evidenced by its wide applicability in construction, ventilation, manufacturing processes, auto washes, hospitals and other fields.

The wall of a support-bead tubing can be quite thin to minimize overall weight. The thin wall also improves flexibility of the tubing. This light weight and flexibility for the tubing is an important feature, for example, in an inhalator tube to provide a patient with more comfort during oxygen delivery. Two other features of known thin single-wall support-bead or bead-reinforced tubing are transparency and smoothness of bore. Transparent plastic material permits inspection of the fluid coursing through the tube, to detect, for example, the presence of moisture in an anesthetic or patient oxygen delivery application. A smooth inner surface of such a tube is desirable to keep the tube free from deposits of contaminants and to discourage non-laminar flow. That is, the smooth bore of the tube promotes a low rate of fluid pressure drop along a length of the tubing, for example, between a breathing assistance machine and patient using such a machine.

U.S. Pat. No. 3,910,808 to Carlson, assigned to the same assignee as this application, discloses apparatus for forming such thin-walled, flexible, crush resistant support-bead tubing having a single wall. Carlson discloses means for extruding a plastic strip having a longitudinal rib, and winding means for helically winding the strip about an axis to produce a corrugated flexible tubing having a smooth bore.

U.S. Pat. No. 5,454,061 to Carlson, also assigned to the same assignee as this application, discloses apparatus for forming single-walled electrically-heated, flexible, crush resistant support-bead tubing. This Carlson patent discloses means for extruding a plastic ribbon, and winding means for helically winding the strip about an axis to produce a thin-walled tube. Upon this thin-walled tube is helically applied at least one electrical resistance heating conductor, and a helical support bead. This tubing substantially satisfies the requirements of many applications which require or are enhanced by the presence of controlled heating of such tubing.

For example, neonatal patients, as well as patients in shock, or patients who are sustained on breathing equipment, are among those who benefit from gas flowing through heat-conditioned tubing. Such is the case because the breathing apparatus usually provided conditioned (i.e., humidified and warmed and possibly medicated and/or oxygenated) air for inhalation by the patient at a temperature close to body temperature. Conventional unheated tubing allows significant heat loss to ambient and cooling of the warmed inhalation air, to the detriment of critical or tenuous patients. cooling of the conditioned air may cause considerable condensation of added humidity within the conventional tubing. It is conventional to use a moisture trap in such apparatus for the purpose of insuring that the patient does not inhale a slug of condensed water from the tubing.

The tubing according to the Carlson '061 patent allows electrical resistance heating to be applied to the tubing to essentially offset this heat loss to ambient from the warmed tidal air flow within the tubing. When properly used, the warmed tidal air flow in the tubing will have an equilibrium condition between its heat loss through the single wall of the tube and heat addition from the heating conductor(s) of the tubing. Thus, the patient will receive warmed conditioned air at substantially the same temperature provided by the inhalation device.

Prior attempts to achieve heating of a tube include providing: a resistance element extending linearly along the tube's axis (U.K. Patent No. 1,448,473 to Grant); fabric tape secured to a wire and applied to the tube (U.K. Patent No. 897,292 to Reik); or resistive wire in a tubing with no crush-resistant or thin-walled features (U.S. Pat. No. 4,038,519 to Foucras; U.S. Pat. No. 4,553,023 to Jameson et al.; and U.S. Pat. No. RE 29,332 to Bilbro et al.). These tubing products and those to be described in more detail in this section have one or more characteristics inconsistent with use in a medical environment. For example, tubing which relies on an adhesive binding for the support bead may deteriorate as a result of repeated sterilization. Materials may be biomedically incompatible, and exteriors are invariably characterized by crevices adjacent to the support bead which can harbor particulate matter and microbes. In addition, the more separate and distinct steps that are required in producing such tubing, the greater the cost, complexity and potential for failure of the product in use.

Another heatable tubing is described by DE 42 44 493A1 to Eilentropp. The '493A1 patent is believed to describe a respiratory tube with a spirally ribbed outer surface upon which electric heating conductors are placed adjacent to the spiral ribs. The heating conductors may be glued on to the outer surface of the tube. The ribs may be formed as a separate smaller tube profile which is then glued to the outer surface of the respiratory tube in a spiral arrangement. With a respiratory tube according to the '493A1 publication, the resistance wires must be separately secured to the outer surface of the tube, requiring a separate manufacturing step. Also, the separate glue may not provide as secure an attachment of the heating conductors to the respiratory tube as would be desired. There is a distinct possibility of imperfect match between the tube and the glue, and the glue also presents a possibility of solvents being released in the medical environment. As previously mentioned, the glue may not endure sterilization as well as the tube itself.

Finally, U.S. Pat. No. 3,686,354, issued to Makin, is believed to provide a thin-walled, flexible, but helically-ribbed collapse-resistant hose for inhalation apparatus. An inner thin-walled flexible tubular member defines a helical groove to which is helically secured an outer heater cable. The electrical heating cable is round in cross-section and is bonded to the outer surface of the tubular member by adhesive or vulcanization. With the inhalation hose according to the '354 patent, the helical heater cable does not become an integral part of the inner tubular member, but instead lays in a helical groove of the inner tubular member, defining a helical crevice on each side of the heater cable. This crevice or pair of crevices may provide an area in which soil and bacteria can escape cleaning and sterilizing efforts. Also, the heat originating at the conductors of the heater cable must be conducted through not only the insulation on this cable but also through to the wall of the inner tube. In fact, these heating conductors would appear to be more directly coupled to the ambient air than to tidal air in the tube.

Another conventional expedient sometimes employed is to provide a heating cable in the configuration of a loop having its two ends terminated adjacent to the inhalation machine. This heating cable is pulled into the flexible tubing leading from the machine to a patient so that it is exposed directly to the tidal air flow in this tubing. Installation of this heating cable into an elongate length of the inhalation tubing requires use of a hooked flexible pulling tool, somewhat like an electrician's or plumber's snake. The electrical connections to this heating cable are terminated at an elbow fitting adjacent to the inhalation therapy machine. Cleaning of the inhalation tubing requires removal and separate cleaning of the heating cable.

An alternative conventional support-bead tubing product is known which has double thin and flexible walls, with one wall inward of a helical support bead, and the other wall outward of the bead. The two flexible walls of this conventional tubing are spaced apart by the support bead and cooperatively define a trapped air space within which the trapped air is substantially stagnant, and provides a desirably high insulation value. Even though this conventional double-walled tubing is an improvement in some uses over the conventional un-heated single-walled support-bead tubing, it does not entirely eliminate heat loss to ambient from warmed tidal air flow in the tubing. In this respect, the conventional double-walled support-bead tubing cannot provide essentially a zero heat loss from tidal air flow along a length of the tubing, as can the electrically heated tubing of Carlson, disclosed in his '061 patent.

No prior product, method of manufacture, or apparatus is known which provides a flexible, support-bead, double-walled, smooth-bore tube having a high insulation value between warmed tidal air and ambient, as well as an electrical resistance heating conductor extending helically along the length of the tube for offsetting heat loss to ambient from warmed tidal air flow in the tube.

SUMMARY OF THE INVENTION

In view of the deficiencies of the related art as discussed above, it is a primary object of the present invention to avoid one of more of the shortcomings of the conventional technology.

It would be an advantage if a flexible, support-bead, double-walled, smooth-bore tubing product having a high insulation value between warmed tidal air and ambient, as well as an electrical resistance heating conductor extending helically along the length of the tube for offsetting heat loss to ambient from warmed tidal air flow in the tube were available. Such a tubing product would provide a combination of the desirably low heat loss to ambient from tidal air flow in the tubing product which conventional double-walled tubing provides, and also would provide the desirably low or zero temperature loss from tidal air flow like the Carlson '061 tubing, because of the electrical resistance heating available from the heating conductor.

To this end, it is an object for this invention to provide a tubing product which provides a flexible, lightweight, crush-resistant double-walled tubing having a pair of radially spaced apart walls confining an insulative dead-air space therebetween, and an electrical heating conductor in the form of a wire helically imbedded in the tubing. A helical support bead is helically wound about the inner one of the two walls and over the heating wire. The outer wall is formed atop the helical support bead and spans from wrap to wrap of this support bead. All of the inner wall, outer wall, and support bead are integral with one another by mutual heat bonding.

It is another object of this invention to provide apparatus and method for inexpensively making a flexible, double-walled, heatable tubing including resistance wire, supporting bead, and tube walls as a unitary body free of adhesive and binders and having both inner and outer surfaces which are substantially smooth.

Yet another object for this invention is to provide such a flexible, double-walled tubing product in which both of the inner and outer walls are pre-disposed to bow outwardly when the tubing is bent. Thus, the bore of the tubing product remains substantially smooth around both the outside and inside of bends in this product.

These and other objects are achieved by the present invention which provides apparatus for combining a thin, film-like first ribbon, an electrical resistance heating conductor, a supporting bead, and a thin film-like second ribbon to make a flexible tubing, and provides a method for producing the tubing in a single winding operation. The present invention employs a winding mechanism which accepts in sequence the first ribbon in a molten extruded plastic condition, an electrical heating conductor, an extruded supporting bead in molten plastic condition, and the second ribbon also in molten extruded plastic condition. The first ribbon is helically wrapped so that its edges overlap and simultaneously heat-bond to themselves to form a lap joint. The electrical heating conductor in the form of a resistance wire is helically overlaid at the lap joint and the bead is helically laid atop the wire and heat-bonded to the ribbon at the lap joint. Next, the second ribbon in molten extruded plastic condition is laid atop the helical wraps of the support bead, and spans from wrap to wrap to trap a helical dead-air space having high insulation value between the inner and outer walls of the tubing. Because the two ribbons and support bead are combined while molten in extruded plastic condition and self heat bond to one another, the tubing is unitary and homogeneous (excepting the electrical heating conductor) with no joints which are secured by adhesive or solvent bonding, for example.

According to another aspect, the present invention provides a method of making a double-walled flexible and collapse-resistant insulative plastic tubing having a substantially smooth bore provided by an inner one of two radially spaced apart integral walls trapping a dead-air space therebetween, and an integral helical support bead disposed between the two walls, the method comprising steps of: providing a first extrusion means for simultaneously extruding elongate thermoplastic first and a second ribbons each having respective opposite marginal side edge portions; forming an elongate tubular body by winding the first ribbon on itself with opposite marginal side edge portions thereof overlapped and interbonding to form a helical lap joint; providing second extrusion means for extruding a thermoplastic support bead; winding the support bead helically around and along the elongate tubular body atop the helical lap joint while heat-bonding to the elongate tubular body; winding the second ribbon helically around and along the elongate tubular body spanning from one wrap of the helical support bead to the next with opposite marginal side edge portions thereof overlapped and inter-bonding the overlapped opposite marginal side edge portions to both one another and the support bead; and cooling the tubing.

Still another aspect of the invention provides a method of making a double-walled flexible and collapse-resistant, electrically-heated, insulative plastic tubing having a substantially smooth bore provided by an inner one of two radially spaced apart integral walls trapping a dead-air space therebetween, and an integral helical support bead disposed between the two walls, the method comprising steps of: providing an elongate thermoplastic first ribbon each having respective opposite marginal side edge portions; forming an elongate tubular body by winding the first ribbon on itself with opposite marginal side edge portions thereof overlapped and interbonding to form a helical lap joint; providing at least one elongate electrical resistance heating conductor; wrapping the electrical resistance conductor helically around and along the elongate tubular body at the lap joint; providing a thermoplastic support bead; winding the support bead helically around and along the elongate tubular body atop the helical lap joint while heat-bonding to the elongate tubular body and encapsulating the electrical resistance heating conductor; winding an elongate thermoplastic second ribbon helically around and along the elongate tubular body spanning from one wrap of the helical support bead to the next with opposite marginal side edge portions thereof overlapped and inter-bonding the overlapped opposite marginal side edge portions to both one another and the support bead; and cooling the tubing.

While other melt-extrudable, heat-bondable plastics may be successfully used in the making of tubing product according to this invention, a preferred material is a polyolefin plastomer (i.e., a plastic and elastic polymer) product. This material may be an ethylene alpha-olefin resin primarily intended for blown-film applications in the packaging industry. However, experience with material of this type in making tubing product according to the present disclosure has yielded excellent results, and its optical qualities are such that the tubing product has desirable transparency, clarity, and freedom from yellowing, milkiness, and opacity.

Considering this manufacturing process in greater detail, the inner walls of the tubing are formed by overlapping, heat-bonding and cooling successive wraps of the first flat ribbon as the ribbon is extruded onto a compound mandrel made of several canted and rotationally driven rollers. The present invention provides a unique wire-feeding mechanism to align at least one electrical resistance heating conductor, preferably in the form of a wire, precisely along an edge of a ribbon wrap which is sufficiently cooled to prevent the wire from cutting through the thin molten first ribbon, but while the first ribbon is still warm enough to partially embed the wire in the ribbon. In the case of a tubing product having a pair of electrical resistance heating conductors in parallel, the guide mechanism is used to position the second conductor spaced from and parallel to the first conductor. Preferably, the second conductor is placed in a slight recess which forms adjacent to the opposite side of the lap joint formed by the first ribbon as it wraps on itself. Alternatively, the second conductor may be placed atop this lap joint, or both conductors can be positioned atop the lap joint. In each case, the heating conductors partially embed into the wrapped ribbon which forms the inner wall of the tubing. Thus, the thickness of the portion of the first ribbon which separates the heating conductor(s) from tidal air flow in the tube is small, and the "R" value of this portion of the plastic tube wall is also low.

The support bead is helically applied atop the heating conductors and atop the lap joint in the inner wall of the tubing. This support bead heat-bonds to the first ribbon substantially contemporaneously with placement of the heating conductors on this inner wall of the tubing, thereby surrounding the wire and integrating the ribbon, wire and bead into a unitary structure. Atop the support bead is formed an out wall consisting of a plastic ribbon which spans from wrap to wrap of the support bead. This second ribbon integrally heat inter-bonds with this support bead. The inner wall, support bead, and outer wall cooperatively trap a helical dead-air space between the walls of the tubing, which dead air space has an advantageously high "R" value. Additionally, the support bead has a high "R" value radially outwardly of the heating conductor(s) so that heat which is liberated at these conductors from flow of electric current therethrough has a much higher conductivity into the tidal air flow in the tubing than it does to ambient.

The advantages and features of the present invention will be better understood after a reading of the following detailed description of three particularly preferred exemplary embodiments of the invention in conjunction with the appended drawing Figures, in which the same reference numerals are used throughout the drawing Figures to identify the same feature, or features which are analogous in structure or function.

BRIEF DESCRIPTION OF THE DRAWINGS

FIG. 5 is a fragmentary elevation view, partly in cross section taken at line 5—5 of FIG. 4, and showing a step in the manufacturing method for a tubing product embodying the present invention;

FIG. 6 is a fragmentary axial view, partly in cross section, similar to FIGS. 3 and 4, but showing a subsequent step in the method of making a tubing product according to the invention;

FIG. 7 provides a fragmentary longitudinal cross sectional view of a tubing product embodying the present invention, and illustrates the sequential steps in making this tubing product according to the present invention;

FIGS. 8 and 9 provided fragmentary cross sectional views of alternative embodiments of a tubing product embodying the present invention;

FIG. 10 provides a longitudinal cross sectional view of a length of the tubing product bent so as to illustrate how the walls of the product bow outwardly to maintain a smooth bore for the tubing;

FIG. 11 is a fragmentary cross sectional view taken at line 11—11 of FIG. 1, and showing the configuration of an extrusion die used in simultaneously making both an inner wall and an outer wall of the tubing product embodying the present invention.

FIG. 12 provides a fragmentary schematic view similar to a portion of FIG. 2, but showing an alternative embodiment of the tubing product invention in which electrical resistance heating conductors are in the form of ribbon conductors; and FIG. 13 is a fragmentary cross sectional view similar to FIGS. 8 and 9, but showing the alternative embodiment of the tubing product made according to the illustration of FIG. 12.

DETAILED DESCRIPTION OF EXEMPLARY EMBODIMENTS OF THE INVENTION

Figure 1:
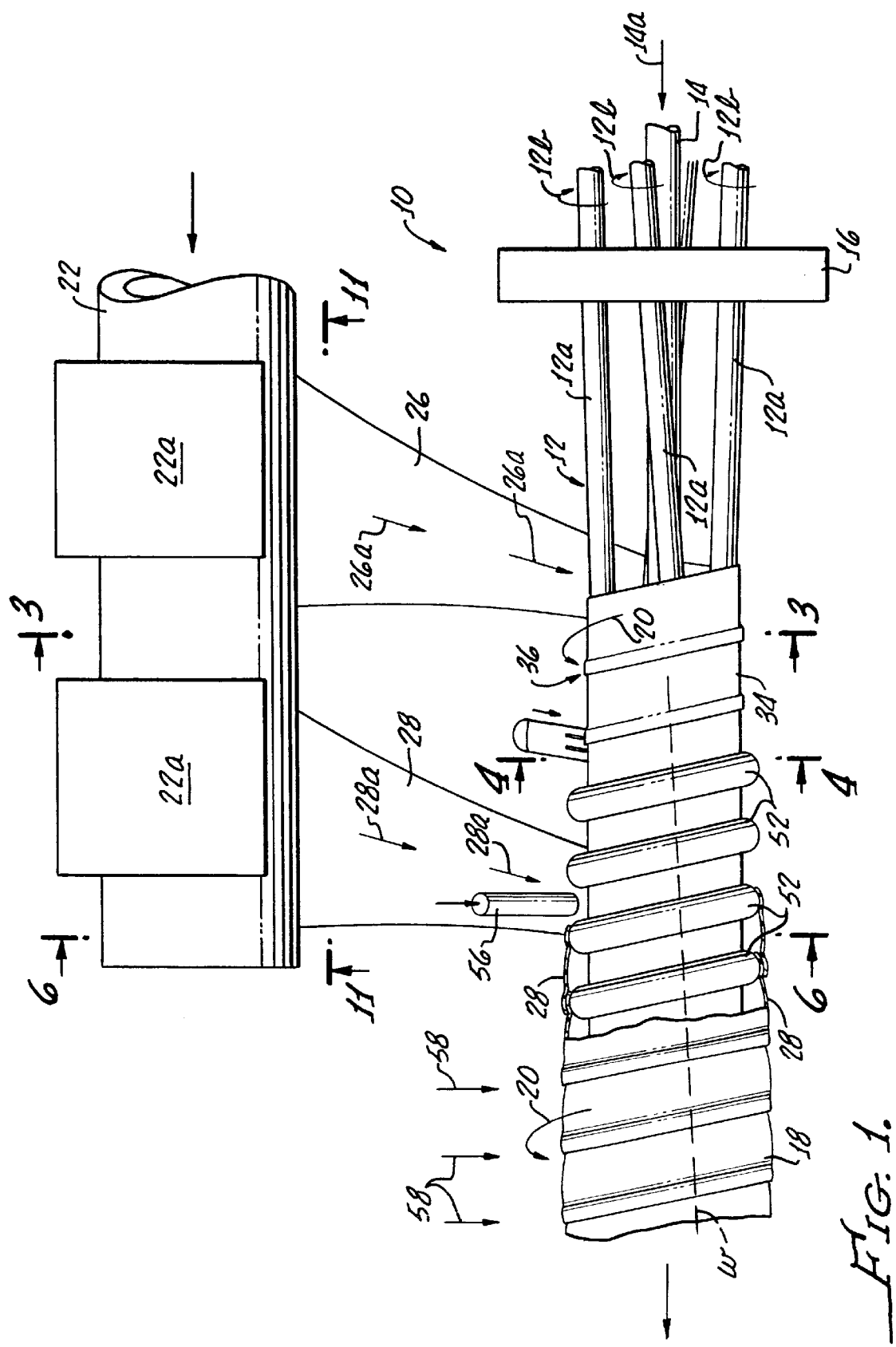
FIG. 1 is a schematic elevation view illustrating an apparatus for practicing a manufacturing method to make a tubing product, both in accord with features of an exemplary embodiment of the invention. In this view parts of the apparatus used in practicing the manufacturing method are relocated for clarity of illustration.

The manufacturing apparatus and method of making a tubing product embodying the present invention, as well as the tubing product itself, are illustrated in the appended drawing figures. FIG. 1 illustrates the manufacturing apparatus 10 including a compound winding mandrel 12 made up of plural power-driven winding rollers 12a. The winding rollers 12a in this case are four in number and are arrayed at 90° to one another around a cooling water tube 14 in a bearing plate 16. All of the winding rollers 12a rotate in synchronization in a clockwise direction when viewed from the right end of FIG. 1, noting the rotation arrows 12b. In this case, the bearing plate 16 of compound mandrel 12 includes spherical bearing inserts (not shown).

The spherical bearing inserts of the plate 16 allow this plate to be positioned with a slight relative rotation with respect to the location of corresponding individual drive shafts from a common gear box (not shown) which provides the driving power for the rollers 12a. These drive shafts are coupled individually to the rollers 12a using universal joints adjacent to the gear box. The drive shafts at the gear box are at a larger diameter, so that the rollers 12a cooperatively are slightly relatively conical (i.e., converge toward an apex to the left of bearing plate 16, viewing FIG. 1). The slight relative rotation of bearing plate 16 relative to the gear box also provides a slight skew (i.e., slight helix angle) to the winding rollers 12a. The helix angle of the winding rollers 12a is opposite to the direction of their rotation, so that the surface velocity vectors of these rollers will have a slight axial component to the left as seen in FIG. 1. This axial velocity component from the winding rollers 12a, as well as their rotation (indicated by arrows 12b) results in the tubing product 18 rotating as is indicated by arrow 20, and having an axial velocity, indicated on the FIG. 1 by arrowed numeral 20a.

In order to provide the three molten plastic elements which are combined on mandrel 12 to form the tubing product 18, two melt extruders (not shown) are employed. Respective extruder heads 22 and 24 are seen in phantom in FIG. 2, and head 22 is seen in the background of FIG. 1 slightly behind the plane of the Figure. These extruder heads typically have strap-on electrical heater jackets to controllably maintain them at an appropriately elevated temperature. Two of the heater jackets 22a, are seen attached to head 22. Extruder head 24 has similar heater jackets, although these are not illustrated in the drawing Figures. Further considering extruder head 22, it is seen in FIG. 1 that a first ribbon 26 and a second ribbon 28 issue from this extruder head, and are combined into the tubing product 18, as will be explained further. However, considering FIG. 1 and FIG. 11 together in greater detail, it will be seen that the ribbons 26 and 28 issue from respective slots 30 and 32 at extruder head 22. These slots 30 and 32 have a thickness ($t_1$ or $t_2$, respectively) which is much greater than that of the ribbons 26 and 28 as they are employed to actually make the tubing product 18. The slots 30 and 32 also have a respective width ($L_1$ or $L_2$, respectively) which is also much greater than the ribbons at the mandrel 12. The slots 30 and 32 are separated by a spacing "S" which is not necessarily the same as the spacing between the ribbons 26 and 28 as applied to the tubing product 18.

Thus, it is seen that the ribbons 26 and 28 both neck down in area and increase in velocity as they move from the extruder head 22 to the mandrel 12 for use in making the tubing product 18. Accordingly, on FIGS. 1, 2, and 11, the ribbons have added velocity arrows 26a, or 28a, which by their length at particular locations give a general idea of the velocity of the ribbons 26 and 28. Each ribbon 26 and 28 has respective opposite side edges.

Figure 2:
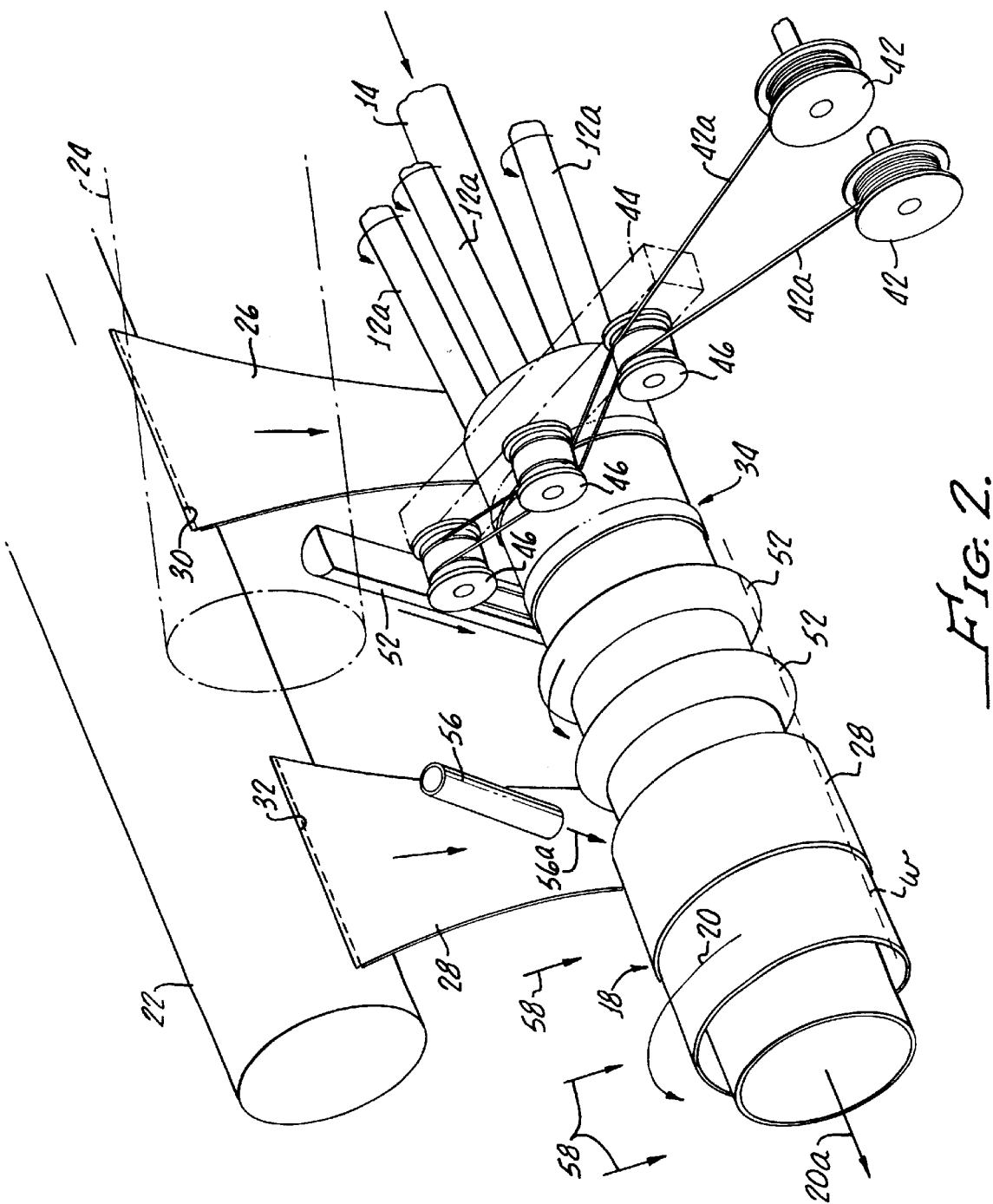
FIG. 2 provides another schematic view showing the manufacturing apparatus and tubing product made using this apparatus according to features of the exemplary embodiment of the invention seen in FIG. 1. Also in this view parts of the apparatus used in practicing the manufacturing method are relocated for clarity of illustration.
Figure 3:
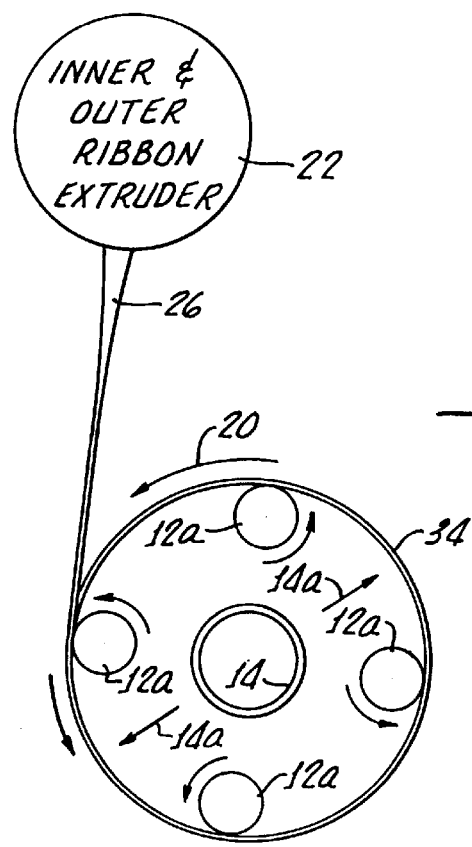
FIGS. 3 and 4 are fragmentary axial views, partly in cross section, showing steps in the method of making a tubing-product according to the invention.

Ribbon 26 is wrapped about the winding rollers 12a and is advanced helically toward the left, viewing FIGS. 1, 2, and 3, so that it encircles the rollers 12a and wraps upon itself with a certain overlap, as best seen in FIG. 7, to form a thin-walled tubular body 34. Adjacent wraps of the ribbon 26 heat-bond to one another to define a continuous helical lap joint 36 cooperatively defined by overlapped opposite side edges and interbonded marginal side edge portions of the ribbon 26. The thin-walled tubular body (and tubing product 18) are formed in an elongate water trough (not shown) extending from adjacent to the bearing plate 16 in the direction of arrow 20a. The depth of water in this trough is controlled so that about half of the tubular body 34 and tubing product 18 is within the water bath. In order to clarify this water depth for the reader, the surface of the water is indicated by a dashed line "w" along the path of tubing product 18. As will be seen, additional cooling water flow is provided in a controlled manner to form and cool the tubing product 18.

Particularly, cooling water tube 14 delivers a spray of water (indicated with arrows 14a) onto the inner surface of the tubular body 34 as it is being formed from wraps of ribbon 26. As will be seen, this cooling water spray first chills the inner surface of the ribbon 26 while simultaneously applying a slight outward pressure because of the momentum of the water jets impinging on the inner surface of the thin-walled tubular body 34 as the molten plastic cools additionally. Consequently, the ribbon 26 is bowed slightly outwardly between its side edges as it wraps on the winding rollers 12a. A result of this slight bow of ribbon 26 will be seen to be a tendency of this ribbon to bow outwardly when the tubing product 18 is bent, as will be further explained by reference to FIG. 10.

Figure 4:
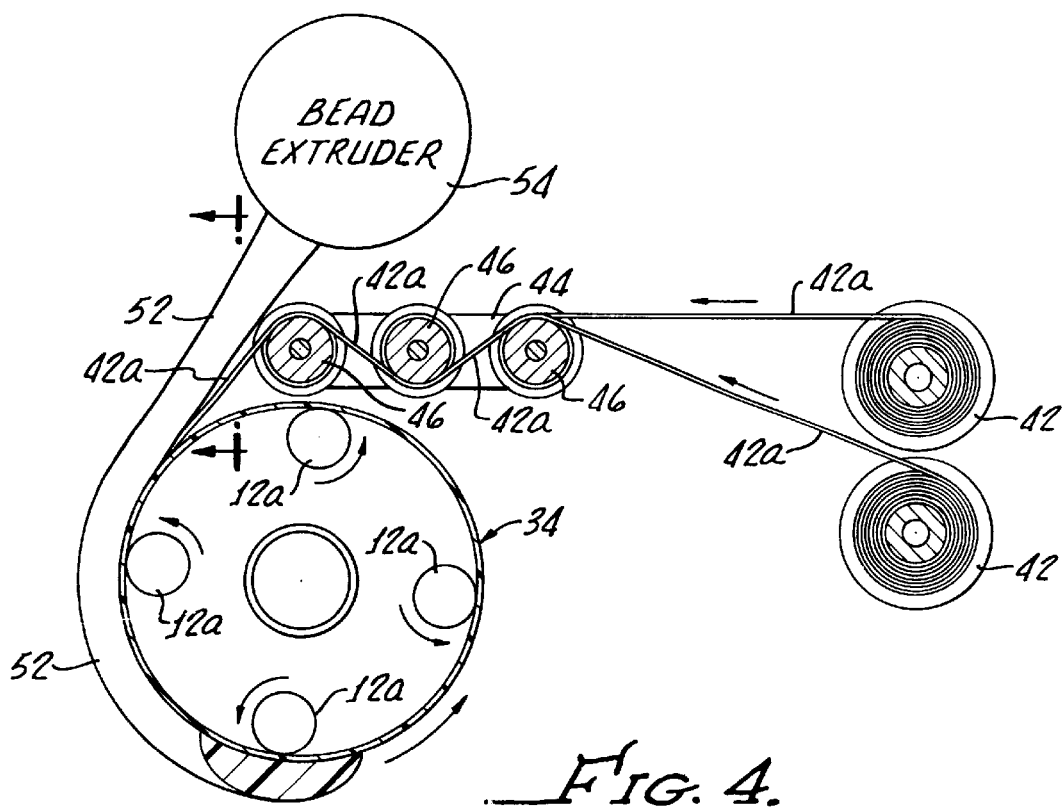

Still viewing FIGS. 1, 2, and 4, it is seen that in order to feed one or two resistance heating conductors into the tubing product 18, apparatus 10 includes wire feeding device 38. This device 38 employs at least one and possibly two payout mechanisms 40 each for rotationally holding a spool 42 of wire 42a. The wire held on these spools is preferably a copper wire. Surprisingly, even though copper wire is not usually considered to be a resistance type of heating conductor, in this application, the two parallel heating conductors 42a when formed of copper will provide the ability to dissipate the desired level of heating, with the desirably low-voltage heating power supply which is to be used in practice. Alternatively, the wires 42a may be made of a more ordinary round resistance heating conductor type of wire. In such a case, a conventional nickel chromium alloy may be used to make the wires 42a. Still alternatively, the resistance heating conductors 42a may be made in a ribbon configuration.

The device 38 includes a beam 44 carrying three grooved rollers 46. Each of the rollers 46 includes a pair of opposite side flanges 48 preventing the wires 42a from slipping off the rollers. Also, between the flanges 48, each roller 46 defines a pair of spaced apart grooves 50, the spacing of which is selected to precisely space apart the wires 42a when a pair of such wires are used in the tubing product 18.

Wires 42a are shown in FIGS. 1, 2, 4, and 5 feeding onto the outer surface of the thin-walled tubular body 34 circumferentially. The first ribbon 26 from which this thin-walled tubular body 34 is formed is at this time formed partially solidified, but is still partially molten. Consequently, the rotation (arrow 20) of the thin-walled tubular body 34 is sufficient to provide traction and to pull in the wires 42a. However, at the same time the wires 42a partially embed into this thin-walled tubular body 34.

Almost contemporaneously with the wires 42a winding onto the thin-walled tubular body 34, a molten support bead 52 is applied over the lap joint 36, and over the conductors 42a. Support bead 52 originates with the second melt extruder (not seen) the extruder head 24 of which is seen in FIGS. 2, and 4. Compared to the mass of the ribbon 26, the support bead 52 is quite massive and carries a comparatively large amount of thermal energy. The support bead 52 heat bonds to the outside of the thin-walled tubular body 34 trapping the conductors 42a, and heat from this bead insures that the overlapped marginal side edge portions of the ribbon 26 are securely heat bonded to one another.

Next, the second ribbon from extruder head 22 (i.e., ribbon 28) is applied over the wraps of support bead 52, spanning from one wrap to the next so as to define an outer wall for the tubing product 18. As is seen in FIG. 7, this second molten ribbon 28 is applied so that a trailing marginal edge portion at side edge 28b (i.e., with reference to the direction of movement of tubing product 18, indicated by arrow 20) is wrapped slightly around the support bead 52. The opposite marginal edge portion (i.e., at the leading side edge 28c opposite to side edge 28b of this ribbon 28 in the direction of arrow 20a). laps and inter-bonds with the marginal edge portion adjacent to side edge 28b so that the edge 28c is "hidden" just to the right of the peak of the support bead, viewing FIG. 7. This "hiding" of the outer edge 28c of ribbon 28 provides a tubing product 18 which is smoother to the touch, and which is free of loose or projecting edges of the outer ribbon 28 which might be caught or lifted up by an edge (such as the edge of a table, for example) as the tubing product is pulled across this edge.

As the second ribbon 28 is wrapped atop the support bead 52, a small tubular conduit 56 directs a jet of pressurized air 56a into the space 56b formed cooperatively by the inner first ribbon 26, the adjacent wraps of support bead 52, and the ribbon 28 being applied. The jetting pressurized air causes the ribbon 28 to bow slightly outwardly, as is seen in the drawing figures.

Next, jets of water are applied from above, indicated by arrows 58, which in combination with the water in the trough partially surrounding the tubing product 18, provide cooling and solidification of the product 18. As will be appreciated, because the ribbons 26 and 28 are wrapping on the mandrels 12 simultaneously as the tubing 18 is advancing, these ribbons form the same helix angle.

The resulting tubing product 18 is shown in more detail in FIG. 10. FIG. 10 illustrates tubing product 18 in a flexed condition with the inner and outer walls (i.e., ribbons 26 and 28), bead 52 and wires 42a in cross-section. This Figure, shows how tubing product 18 may be bent to a small radius. On the inside of this bend radius, the inner wall 26 buckles outwardly between beads 52, and with the outer wall 28 also buckles outwardly between these support beads 52.

As is seen in FIG. 7, the electrical heating conductors (i.e., wires 42a) may be placed one adjacent to the outer edge of ribbon 26 at lap joint 36, and the other atop of this lap joint. Viewing now FIGS. 8 and 9, two alternative embodiments of the present invention are presented. Because these alternative embodiments differ from one another and from the first-described embodiment only with respect to the placement of wires 42a, in order to obtain reference numerals for use in describing the embodiments of FIGS. 8 and 9, features which are the same, or which are analogous in structure or function to those described above, are referenced with the same numeral used above.

FIGS. 8 and 9 show that alternative embodiments of the tubing product 18 may be made with the wires 42a on opposite sides of the lap joint 36 (FIG. 8), or with both wires 42a atop of this lap joint 36 (FIG. 9). An advantage of the embodiment shown in FIG. 8 is that both heating conductors are separated from tidal air flow in the tubing product by a thickness of ribbon 26 which is no more than one ribbon-thickness (recognizing that the wires 42a embed somewhat into the molten ribbon 26 as they are wrapped about the thin-walled tubular body 34—recalling the description above of FIGS. 1 and 2). This construction gives the lowers possible "R" rating between the heating conductors and the tidal air flow within the tubing product 18. In other words, the heating conductors are most directly tied to the tidal air flow in heat transfer relation with the construction as seen in FIG. 8.

The construction of FIG. 7 is next most desirable because one of the conductors is separated from tidal air flow in the tubing product by a thickness of ribbon 26 which is no more than one ribbon-thickness. However, the other conductor is atop lap joint 36, and is separated from tidal air flow by about twice the "R" value as the other conductor.

An alternative construction which is next most preferred is seen in FIG. 9. In this construction, both wires 42a are atop of the lap joint 36. In this case, the "R" value between each conductor and the tidal air flow in tubing product 18 would be equal, and would be about twice that for the construction of FIG. 8. On the other hand, in each case, the resistance heating conductors 42a are insulated from ambient by the mass of support bead 52.

All of these considerations of "R" value between the conductors 42a and the tidal air flow in tubing product 18 must be viewed with the understanding that the "R" values between the tidal air flow and ambient for all of the embodiments of the tubing product 18 are much greater. That is, the tidal air flow is effectively insulated and isolated so far as heat loss to ambient is concerned. This insulation of the tidal air flow from heat loss to ambient is provided by the insulating value of the support bead, and by the trapped "dead-air" space 56b between walls 26 and 28.

An advantage of the tubing product 18 seen in this application is that the two conductors 42a may be used to form opposite sides of a heating circuit. That is, electrical connections to the conductors 42a may be made at one end of a length of the tubing product (for example, adjacent to an inhalation therapy machine), while the opposite ends of the conductors 42a are simply connected together at the end of the tubing adjacent to the patient. By providing a conventional temperature sensor exposed to the tidal air flow delivered to the patient, and a heater control circuit, a sufficient heating electrical current flow can be provided in the conductors 42a to equilibrate the heat loss from the tidal air flow to ambient.

That is, as described, the tubing product 18 has a particular advantage for use with such medical patient ventilator or inhalation therapy apparatus. It is a particular advantage that the electrical connections to the tubing can be effected at the proximal end near the ventilator. At the distal end of the length of tubing near the patient, connection of the conductors 42a to one another is all that is needed to complete the electrical heating circuit of the tubing 18. The voltage level and/or current level of electrical power supplied to the tubing 18 can be lower than in any previous product in order to achieve equilibrium of heat supplied to heat loss because of the low "R" value from heating conductors 42a to tidal air flow combined with the very good "R" value of the tubing product between tidal air flow and ambient. It is recognized in medical environments that reduction of voltage levels used in medical devices is an advantage because of the reduced risk of shock or electrocution to both medical personnel and to patients. For this reason, the reduction of heating voltage requirement made possible by the present invention is an important consideration. Also, the reduced heat loss from the tidal air flow to ambient provided by the present tubing product, as well as the fact that temperature equilibrium of this tidal air flow can be achieved, means that moisture will not so readily condense in the tube between inhalation therapy and other such machines and patients. As a result, the risk of a patient inhaling a slug of condensed water is greatly reduced.

Viewing now FIG. 12, an alternative embodiment of the tubing product invention is depicted. This alternative tubing product invention differs from those already described only with respect to the configuration of the electrical resistance heating conductors. Accordingly, the same reference numerals used above are used in describing the embodiment of FIG. 12. Viewing FIG. 12, it is seen that the wire feeding device 38 of apparatus 10 in this case includes rollers 46 which have two relatively wide grooves 46. The grooves 46 in this case are configured to receive and guide electrical resistance heating conductors 42a of a flat ribbon-conductor configuration. FIG. 13 shows the tubing product 18 produced according to the manufacturing method and apparatus illustrated in FIG. 12. As can be seen, the two ribbon conductors 42a are disposed adjacent to the lap joint 36 defined by wraps of the first ribbon 26. It will be noted that because of the increased area of the heating conductors 42a confronting the tidal air flow in tubing 18 of FIGS. 12 and 13, the "R" value between the heating conductors and the tidal air flow would be even lower than that obtained with round heating wire.

While four exemplary forms of the tubing product 18 have been shown in the drawings and described, variations from the exemplary forms will be apparent to those skilled in the art. The invention therefore should not be construed as being limited to the specific forms shown and described, but instead is limited only by the spirit and scope of the appended Claims, giving full cognizance to equivalents in all respects.

What is claimed is:

1. A method of making a double-walled flexible and collapse-resistant insulative plastic tubing having a substantially smooth bore provided by an inner one of two radially spaced apart integral walls trapping a dead-air space therebetween, and an integral helical support bead disposed between the two walls so that the two integral walls and helical support bead are formed simultaneously and all have a common helix angle, said method comprising steps of:

simultaneously providing an elongate thermoplastic first ribbon and an elongate thermoplastic second ribbon each having respective opposite marginal side edge portions;

first, forming an elongate tubular body by winding said first ribbon on itself with opposite marginal side edge portions thereof overlapped and interbonding to form a helical lap joint;

simultaneously providing a thermoplastic support bead;

secondly, winding said support bead helically around and along said elongate tubular body atop said helical lap joint while heat-bonding said support bead to said elongate tubular body;

thirdly, winding said second ribbon helically around and along said elongate tubular body while spanning from one wrap of said helical support bead to the next, while bowing radially outwardly, and while heat-bonding at overlapped opposite marginal side edge portions thereof itself and to said support bead; and cooling said tubing;

whereby upon the tubing being bent, the flexibility of the tubing is improved by a radially outward bowing of the second ribbon at the inside of such bend.

2. The method of claim 1 further including the steps of:

providing at least one elongate electrical resistance heating conductor;

wrapping said electrical resistance conductor helically around and along said elongate tubular body at said lap joint; and using said thermoplastic support bead to encapsulate said electrical resistance conductor.

3. The method of claim 1 further including the step of: configuring said at least one elongate electrical resistance conductor to be of ribbon-conductor shape.

4. The method of claim 1 further including the step of: configuring said at least one elongate electrical resistance conductor to include a pair of conductors in spaced apart parallel relationship extending helically about and along said tubing.

5. The method of claim 4 further including the step of: disposing said pair of conductors on opposite sides of and adjacent to said lap joint.

6. The method of claim 4 further including the step of: disposing said pair of conductors one adjacent to said lap joint and one atop said lap joint.

7. The method of claim 4 further including the step of: disposing said pair of conductors both atop of said lap joint.

8. A continuous single-process method of making a double-walled flexible and collapse-resistant, electrically-heated, insulative plastic tubing having a substantially smooth bore provided by an inner one of two radially spaced apart integral walls trapping a dead-air space therebetween, and an integral helical support bead disposed between the two walls, said method comprising steps of:
  providing a first melt-extrudate in the form of an elongate thermoplastic first ribbon having opposite marginal side edge portions;
  simultaneously forming an elongate tubular body by winding said first ribbon on itself with said opposite marginal side edge portions thereof overlapped and interbonding to form a helical lap joint;
  simultaneously providing at least one elongate electrical resistance heating conductor;
  simultaneously wrapping said electrical resistance conductor helically around and along said elongate tubular body at said lap joint;
  simultaneously providing a second melt-extrudate in the form of a thermoplastic support bead;
  simultaneously winding said support bead helically around and along said elongate tubular body atop said helical lap joint while heat-bonding to said elongate tubular body and encapsulating said electrical resistance heating conductor;
  simultaneously providing a third melt-extrudate in the form of an elongate thermoplastic second ribbon, and winding said second ribbon helically around and along said elongate tubular body spanning from one wrap of said helical support bead to the next, while bowing radially outwardly, and with opposite marginal side edge portions thereof overlapping and inter-bonding to both one another and said support bead so that said first ribbon, said second ribbon, said helical support bead, and said electrical resistance heating conductor all define a common helix angle relative to said tubing; and
  cooling said tubing;
  whereby upon the tubing being bent, the flexibility of the tubing is improved by a radially outward bowing of the second ribbon at the inside of such bend.

9. The method of claim 8 further including the step of: providing two of said first melt extrudate, said second melt extrudate, and said third melt-extrudate simultaneously from a single melt extruder.

10. The method of claim 8 further including the step of: configuring said at least one elongate electrical resistance conductor to be of ribbon-conductor shape.

11. The method of claim 8 further including the step of: configuring said at least one elongate electrical resistance conductor to include a pair of conductors in spaced apart parallel relationship extending helically about and along said tubing.

12. The method of claim 11 further including the step of: disposing said pair of conductors on opposite sides of and adjacent to said lap joint.

13. The method of claim 11 further including the step of: disposing said pair of conductors one adjacent to said lap joint and one atop said lap joint.

14. The method of claim 11 further including the step of: disposing said pair of conductors both atop of said lap joint.

15. A method of making a double-walled flexible and collapse-resistant insulative plastic tubing, said method comprising steps of: providing an elongate thermoplastic first ribbon and an elongate thermoplastic second ribbon each having respective opposite marginal side edge portions; forming an elongate tubular body by winding said first ribbon on itself with opposite marginal side edge portions thereof overlapping and interbonding to form a helical lap joint; providing a thermoplastic support bead and winding said support bead helically around and along said elongate tubular body atop said helical lap joint while simultaneously heat-bonding said support bead to said elongate tubular body; winding said second ribbon helically around and along said elongate tubular body while spanning said second ribbon from one wrap of said helical support bead to the next, bowing said second ribbon radially outwardly, and heat-bonding said second ribbon at overlapped opposite marginal side edge portions thereof both to itself and to said support bead; and cooling said tubing while retaining said outward bow of said second ribbon in said span thereof between wraps of said support bead.

16. The method of claim 15 further including steps of: providing at least one elongate electrical resistance heating conductor; wrapping said electrical resistance conductor helically around and along said elongate tubular body at said lap joint; and using said thermoplastic support bead to encapsulate said electrical resistance conductor.

17. The method of claim 15 further including the step of: configuring said at least one elongate electrical resistance conductor to be of ribbon-conductor shape.

18. The method of claim 17 further including the step of: configuring said at least one elongate electrical resistance conductor to include a pair of conductors in spaced apart parallel relationship extending helically about and along said tubing.

19. A method of making a double-walled flexible and collapse-resistant, electrically-heated, insulative plastic tubing having a substantially smooth bore provided by an inner one of two radially spaced apart integral walls trapping a dead-air space therebetween, and an integral helical support bead disposed between said two walls, said method comprising steps of: providing an elongate molten thermoplastic first ribbon having opposite marginal side edge portions; forming an elongate tubular body by winding said first ribbon on itself with said opposite marginal side edge portions thereof overlapping and interbonding to form a helical lap joint; providing at least one elongate electrical resistance heating conductor; wrapping said at least one electrical resistance conductor helically around and along said elongate tubular body at said lap joint; providing an elongate molten thermoplastic support bead; winding said support bead helically around and along said elongate tubular body atop said helical lap joint while said support bead heat-bonds to said elongate tubular body and encapsulates said electrical resistance heating conductor; providing an elongate molten thermoplastic second ribbon, and winding said second ribbon helically around and along said elongate tubular body while spanning said second ribbon from one wrap of said helical support bead to the next, bowing said second ribbon radially outwardly, and interbonding opposite marginal side edge portions of said second ribbon to one another and to said support bead; and cooling said tubing while retaining said bowing of said second ribbon in the span thereof between adjacent wraps of said support bead.

20. The method of claim 19 further including the step of: providing simultaneously from a single melt extruder at least a selected two of the group including: said first elongate molten thermoplastic ribbon, said second elongate molten thermoplastic ribbon, and said elongate molten support bead.

21. The method of claim 19 further including the step of: configuring said at least one elongate electrical resistance conductor to be of ribbon-conductor shape having a pair of conductors and an insulative jacket encompassing said pair of conductors.

22. The method of claim 21 further including the step of: configuring said ribbon conductor to include said pair of conductors in spaced apart parallel relationship extending helically about and along said tubing.

* * * * *